United States Patent
Fitts et al.

[19]

[11] Patent Number: 6,096,060
[45] Date of Patent: Aug. 1, 2000

[54] BIOABSORBABLE THREADED SOFT TISSUE ANCHOR SYSTEM

[75] Inventors: Steven E. Fitts, Ridge Manor; A. Frank Trott, Largo; James Gross; Lloyd Diamond, both of Tampa; Steven T. Jones, Bradenton; Sharon K. Anderson, St. Petersburg, all of Fla.

[73] Assignee: Linvatec Corporation, Largo, Fla.

[21] Appl. No.: 09/315,415

[22] Filed: May 20, 1999

Related U.S. Application Data

[60] Provisional application No. 60/082,183, Apr. 17, 1998.

[51] Int. Cl.⁷ .................................................. A61B 17/04
[52] U.S. Cl. ............................................. 606/232; 606/73
[58] Field of Search ............................. 606/232, 73, 104, 606/72, 76, 77; 128/898

[56] References Cited

U.S. PATENT DOCUMENTS

| | | |
|---|---|---|
| 2,414,882 | 1/1947 | Longfellow . |
| 4,175,555 | 11/1979 | Herbert ................................ 128/92 B |
| 4,463,753 | 8/1984 | Gustilo . |
| 4,507,817 | 4/1985 | Staffeld . |
| 4,632,100 | 12/1986 | Somers et al. . |
| 4,754,749 | 7/1988 | Tsou .................................. 128/92 YE |
| 4,784,138 | 11/1988 | Sinnett . |
| 4,873,976 | 10/1989 | Schreiber . |
| 4,924,865 | 5/1990 | Bays et al. . |
| 4,963,144 | 10/1990 | Huene . |

(List continued on next page.)

FOREIGN PATENT DOCUMENTS

WO 97/26028  7/1997  WIPO .

OTHER PUBLICATIONS

Product Brochure "Bio-Anchor Shoulder Instability Repair System" Linvatec Corporation, 1996, 2 pages.
Product Brochure "The Revo/Mini-Revo Shoulder Fixation System" Surgicaltechnique, Linvatec Corporation, 1998, 11 pages.
Product Brochure "Biostinger Bioabsorbable Meniscal Fixation" Surgical Technique, Linvatec Corporation, 1998, 6 pages.
Surgical Technique for Suretac, Acufex Microsurgical Inc. 5 pages.
Product Brochure Bankart Tack, Advancing Art and Science in Repair of Bankart Lesions, Bionx Implants Inc, 1998,6 pages.
Product Brochure, "Fastak Shoulder Repair, Surgical Technique", Arthrex 1996, 19 pages.

(List continued on next page.)

*Primary Examiner*—Michael Buiz
*Assistant Examiner*—Kevin Truong
*Attorney, Agent, or Firm*—Gene Warzecha

[57] ABSTRACT

A bioabsorbable soft tissue anchor system comprising a cannulated soft tissue anchor for being turned through soft tissue, and a driver for driving the anchor and method for attaching soft tissue at a selected site of implantation. The soft tissue anchor is an elongated unitary body having a threaded distal section, a non-threaded proximal section, a transverse proximal head and a non-circular axial throughbore. The threaded section has a cancellous-type thread which has a uniform minor diameter, a large pitch and a large major diameter, the distal end of the thread being tapered toward the distal end of the anchor. The proximal end of the threaded section abuts the non-threaded section which is tapered and extends proximally to the transverse head. The anchor is used with a driver having a driving shaft with a pointed tip and a cross-section adapted to engage the anchor's axial throughbore. The driving shaft is longer than the anchor so that the anchor may be placed on the shaft leaving the tip exposed to permit tissue to be pierced and placed adjacent a pre-formed hole at the site of implantation. Simultaneous pushing and turning of the driver will then advance the anchor through the tissue and into the pre-formed hole.

12 Claims, 4 Drawing Sheets

U.S. PATENT DOCUMENTS

| | | |
|---|---|---|
| 5,013,316 | 5/1991 | Goble et al. . |
| 5,152,765 | 10/1992 | Ross et al. . |
| 5,156,616 | 10/1992 | Meadows et al. . |
| 5,209,753 | 5/1993 | Biedermann et al. . |
| 5,258,016 | 11/1993 | Dipoto et al. . |
| 5,259,398 | 11/1993 | Vrespa . |
| 5,261,914 | 11/1993 | Warren . |
| 5,354,299 | 10/1994 | Coleman . |
| 5,370,662 | 12/1994 | Stone et al. . |
| 5,380,334 | 1/1995 | Torrie et al. . |
| 5,423,819 | 6/1995 | Small et al. . |
| 5,456,685 | 10/1995 | Huebner . |
| 5,470,334 | 11/1995 | Ross et al. . |
| 5,492,442 | 2/1996 | Lasner . |
| 5,520,688 | 5/1996 | Lin ............ 606/61 |
| 5,522,843 | 6/1996 | Zang . |
| 5,569,247 | 10/1996 | Morrison . |
| 5,569,252 | 10/1996 | Justin et al. . |
| 5,571,139 | 11/1996 | Jenkins, Jr. . |
| 5,573,548 | 11/1996 | Nazre et al. . |
| 5,591,166 | 1/1997 | Bernhardt et al. . |
| 5,683,401 | 11/1997 | Schmieding et al. . |
| 5,690,677 | 11/1997 | Schmieding et al. . |
| 5,695,497 | 12/1997 | Stahelin . |
| 5,702,398 | 12/1997 | Tarabishy ............ 606/72 |
| 5,720,766 | 2/1998 | Zang et al. . |
| 5,728,116 | 3/1998 | Rosenman . |
| 5,735,851 | 4/1998 | Errico et al. . |
| 5,824,011 | 10/1998 | Stone et al. . |
| 5,868,749 | 2/1999 | Reed ............ 606/76 |
| 5,895,396 | 4/1999 | Day et al. . |

OTHER PUBLICATIONS

Brochure, "Corkscrew Rotator Cuff Repair, Surgical Technique", Arthrex, 1996, 19 pages.

Arthrex Product Catalog, 98/99, pp. 93, 107, 108, 109.

Dyonics Arthroscopic Reconstructive Screw System, 4 pages.

Product Brochure, So E–Z . . . So Secure S.D.Sorb E–Z Tac Implant, A Fixation Revolution For Soft Tissue Reattachment, Surgical Dynamics, 1997, 4 pages.

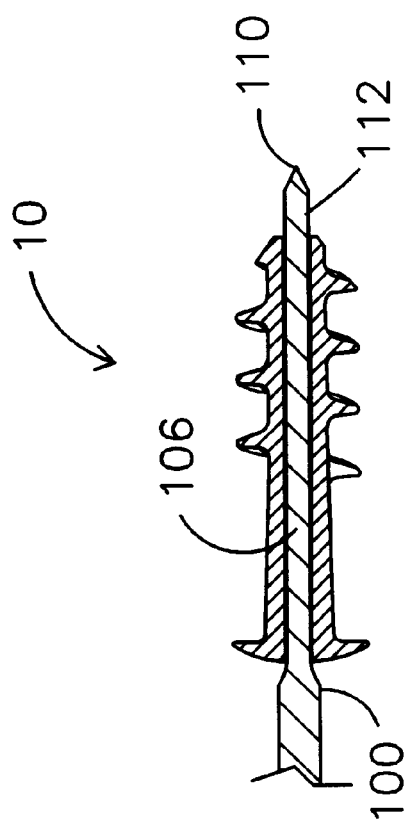
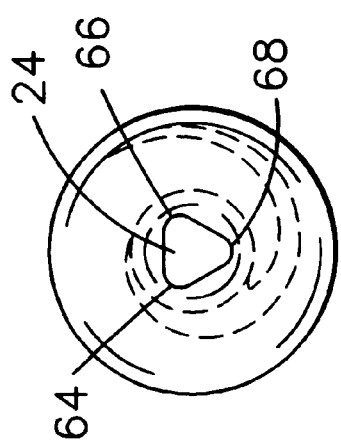
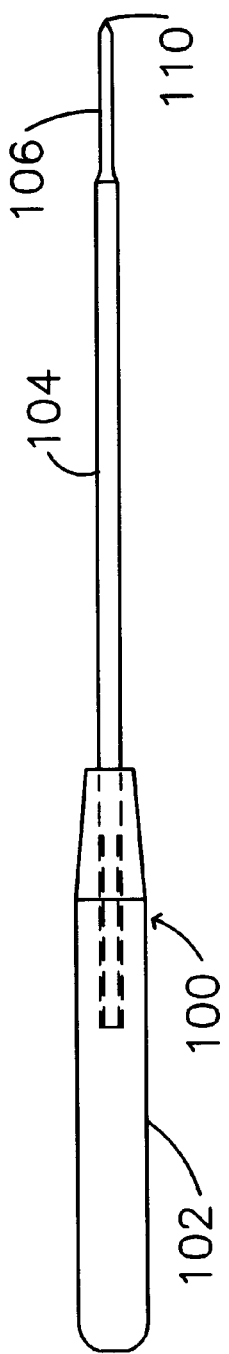
Fig. 3
Fig. 4
Fig. 5

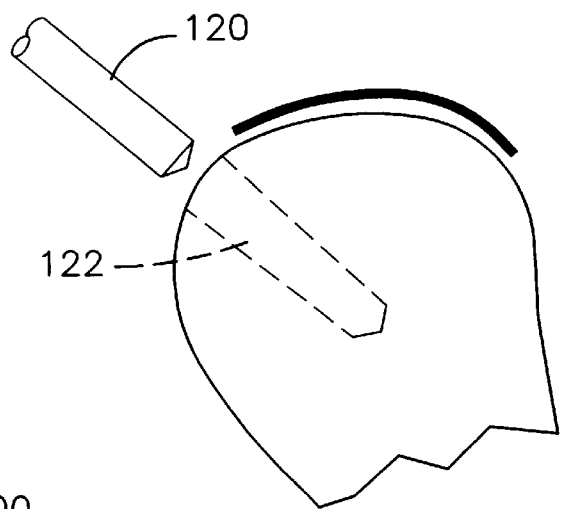
*Fig. 6*
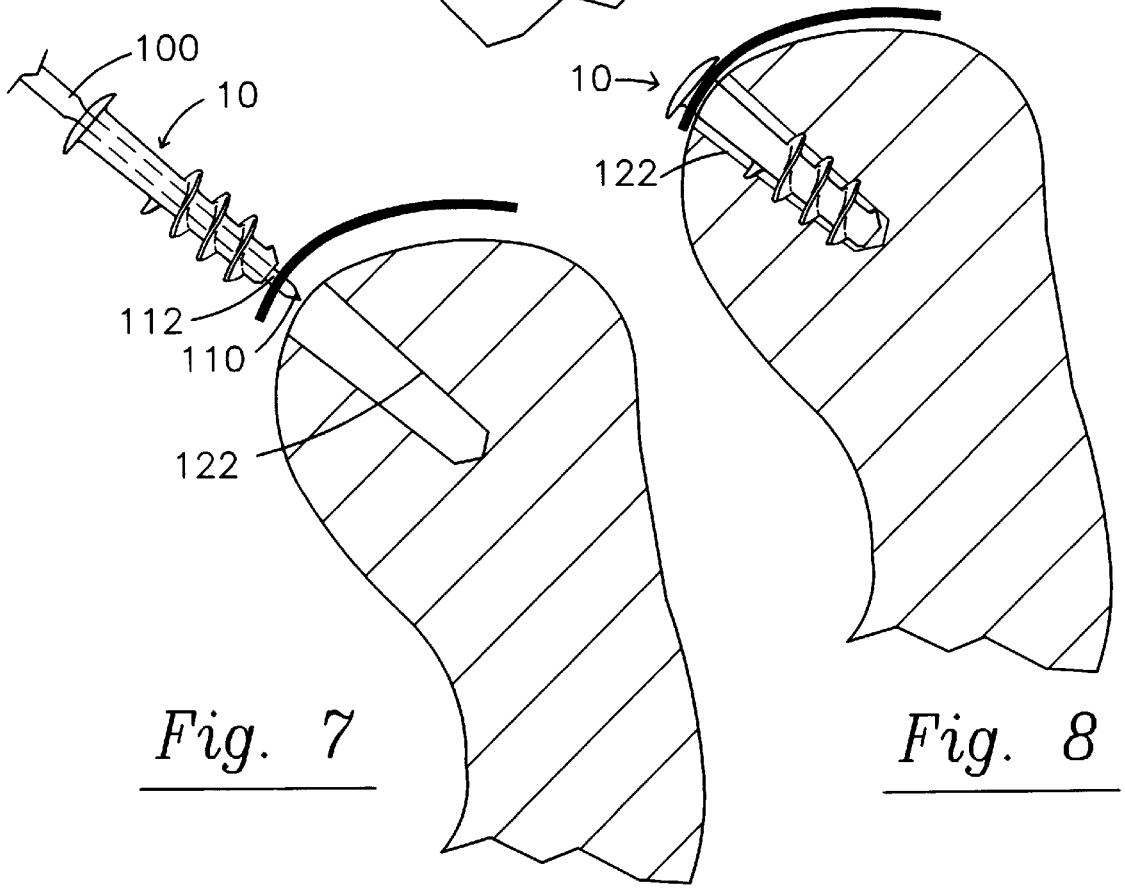
*Fig. 7*
*Fig. 8*

BIOABSORBABLE THREADED SOFT TISSUE ANCHOR SYSTEM

This application claims benefit of Provisional Application 60/082,183, filed Apr. 17, 1998.

BACKGROUND OF THE INVENTION

1. Field of the Invention

The invention relates generally to soft tissue fixation devices. More particularly, the invention relates to threaded fixation devices for securing soft tissue to bone. Still more particularly, the invention relates to sutureless soft tissue fixation devices.

2. Description of the Prior Art

In the course of certain surgical procedures, soft tissue is attached to a selected bone surface either directly, via suture or some type of implant device (i.e. an anchor), or indirectly via an implant device to which suture is attached so it may then be tied to the soft tissue to hold it in place. Such implant devices may be bioabsorbable and generally have a bone-attachment or anchor portion, for securing the device to a selected bone or other firm tissue, and a soft-tissue-attachment portion for securing the soft tissue to the device. It will be understood that the terms "soft" and "bone" are relative and the devices disclosed herein may be used to attach a relatively soft material to a relatively hard material. The term "bone" as used herein thus includes any firm tissue which can anchor the device. The term "base" may be used occasionally herein to refer to such anchoring material. The anchor portion of these soft tissue attachment devices is generally elongated and may be, for example, in the form of a generally cylindrical body having a screw thread, deformable radially extending annular ribs or radially extending, circumferentially spaced, relatively resilient barbs. Some devices have a hollow expandable sleeve, which is inserted into place within a pre-formed hole in a bone, and a solid core which is inserted into the associated sleeve to expand it against the bone wall of the pre-formed hole.

The soft tissue attachment portion of these devices is in the form of a means to hold soft tissue fixed relative to the anchor portion. This holding function is done generally by a suture extending between the anchor portion and the soft tissue, or by another structure. If suture is used, the device is sometimes referred to as a suture anchor with the suture generally being either threaded through an eyelet or other aperture formed into the anchor, or knotted within an aperture on the anchor or otherwise secured to the anchor, prior to the anchor being implanted. If suture is not used, the devices are sutureless in that they employ a transverse structure or head attached to the anchor portion so that the soft tissue is maintained adjacent to the bone surface by a relatively large head attached to one end of a relatively narrow anchor portion.

Anchors may be used to attach soft tissue such as ligaments, tendons, muscles, etc. to a surface from which the soft tissue has become detached. For example, the rotator cuff may be reattached to the humeral head during a shoulder repair. Anchors may also be used to secure soft tissue to supplementary attachment sites for reinforcement. For example, in urological applications anchors may be used in bladder neck suspension procedures to attach a portion of the bladder to an adjacent bone surface. Such soft tissue attachments may be done during either open or closed surgical procedures, the latter being generally referred to as arthroscopic or endoscopic surgery. The terms "arthroscopic" and "endoscopic" may be used interchangeably herein and are intended to encompass arthroscopic, endoscopic, laparoscopic, hysteroscopic or any other similar surgical procedures performed with elongated instruments inserted through small openings in the body.

The prior art includes numerous types of suture anchors adapted to be secured in the bone, sometimes directly in one step and sometimes in pre-drilled or pre-formed holes or tunnels. These anchors are generally "push-in" or "turn-in" type anchors and once placed in bone require that soft tissue be sutured to the anchors. Prior art push-in suture anchors are generally elongated, cylindrical devices having annular ribs or radially extending barbs and are required to be pushed or hammered directly into bone or into a pre-formed bone tunnel (exemplified by U.S. Pat. Nos. 5,102,421 (Anspach, Jr.); 5,141,520 (Goble et al.); 5,100,417 (Cerier et al.); 5,224,946 (Hayhurst et al.) and 5,261,914 (Warren)). Pushing an anchor into place may in some circumstances be undesirable because of potential trauma and damage to surrounding bone tissue, and has limited applicability in certain situations such as, for example, where the location of the bone tunnel or pre-drilled hole is not axially aligned with an arthroscopic portal to permit transmission of the impacting force through an impactor to the anchor. Furthermore, a pushed-in suture anchor is not easily removable without damaging the bone into which it has been placed. Consequently, turn-in or threaded suture anchors are often used as exemplified by U.S. Pat. Nos. 5,156,616 (Meadows et al.) and 4,632,100 (Somers et al.). Such anchors are generally elongated, cylindrical devices having a plurality of threads and a pointed tip. Depending upon the type of threaded anchor, the insertion procedure may enable direct threading of the anchor into the bone or it may sometimes require that a pilot hole first be drilled or formed into the bone, the hole then either enables an anchor to be screwed in or enables threads to be tapped to receive the anchor.

Push-in sutureless soft tissue anchors are known and have a transverse head which enables a user to avoid the suturing step, but these devices are not easily removable. Turn-in sutureless soft tissue anchors are also known and these devices have either a multi-part construction, with the head separate from and not integrally formed with the anchoring body, or are otherwise limited in strength or ease of manufacture and require a relatively complex insertion procedure. Overcoming the disadvantages of prior art devices while making these a device from bioabsorbable materials requires a design which is strong enough to withstand insertion stresses and use prior to absorption by the body.

In procedures utilizing indirect suturing of soft tissue to bone, the suture may either be first anchored by suture anchors to the bone before passing the suture through the soft tissue, or the tissue may first be sutured and the anchor may then be slid down one leg of the suture and then implanted into bone. In procedures utilizing sutureless devices which directly attach soft tissue, the devices are inserted through the soft tissue.

It would be desirable to simplify not only the method used to attach soft tissue to bone in certain surgical procedures but also the manufacture of sutureless soft tissue fixation devices.

It is accordingly an object of this invention to produce a system for inserting threaded soft tissue anchors into bone.

It is also an object of this invention to produce a unitary, threaded sutureless soft tissue anchor.

It is a further object of this invention to produce a bioabsorbable threaded sutureless soft tissue anchor.

It is yet another object of this invention to produce a threaded, sutureless soft tissue anchor which can be embedded into bone while minimizing trauma to the surgical site.

It is another object of this invention to produce a system for the sutureless fixation of soft tissue to bone.

It is yet another object of this invention to produce a sutureless soft tissue fixation system capable of securing soft tissue to a selected site without the need for a guide wire or similar intermediate step.

It is also an object of this invention to produce a sutureless soft tissue fixation system capable of driving into bone a soft tissue anchor made of a relatively soft, preferably bioabsorbable material.

SUMMARY OF THE INVENTION

These and other objects of this invention are achieved by the preferred embodiment disclosed herein which comprises a soft tissue anchor for attaching soft tissue to a hole in a bone. The anchor comprises a cannulated body having a proximal end, a distal end, an axis and an axial throughbore having a non-circular cross-section. The body comprises a threaded distal section extending proximally from the distal end and having a first predetermined length, the distal end of the threaded section being tapered distally. A non-threaded proximal section extends proximally from the threaded distal section, has a second predetermined length and is adapted to compressively contact the soft tissue and a predetermined portion of the wall of the hole in the bone. The anchor has a transverse head at its proximal-most end for seating against the soft tissue.

The invention also comprises a method for attaching relatively soft tissue to a hole in relatively hard tissue. The method comprises the steps of providing a soft tissue anchor such as described above and providing a driver for driving the anchor through soft tissue (i.e. relatively soft material) and into a hole (i.e. relatively hard material). The driver comprises an elongated driving shaft having a cross-section complementary to that of the anchor throughbore, a pointed tip and a length greater than that of the anchor. The method further comprises engaging the soft tissue anchor on the driving shaft, piercing soft tissue with the pointed tip, positioning the pierced soft tissue and tip over the preformed hole and pushing the pointed tip into the hole. Finally simultaneously pushing and turning the driver will advance the anchor into and through the soft tissue until the distal facing surface of the head contacts the soft tissue.

BRIEF DESCRIPTION OF THE DRAWINGS

FIG. 3 is a top plan view of FIG. 1.

FIG. 4 is a side elevational view of a driver for inserting the soft tissue anchor of FIG. 1.

FIG. 5 is an enlarged view of the distal tip of the driver of FIG. 4 shown engaged with the soft tissue anchor of FIG. 1.

FIGS. 6, 7 and 8 are diagrammatic views of sequential steps of the method for attaching soft tissue to bone using the system disclosed herein.

DESCRIPTION OF THE PREFERRED EMBODIMENT

Figure 1:
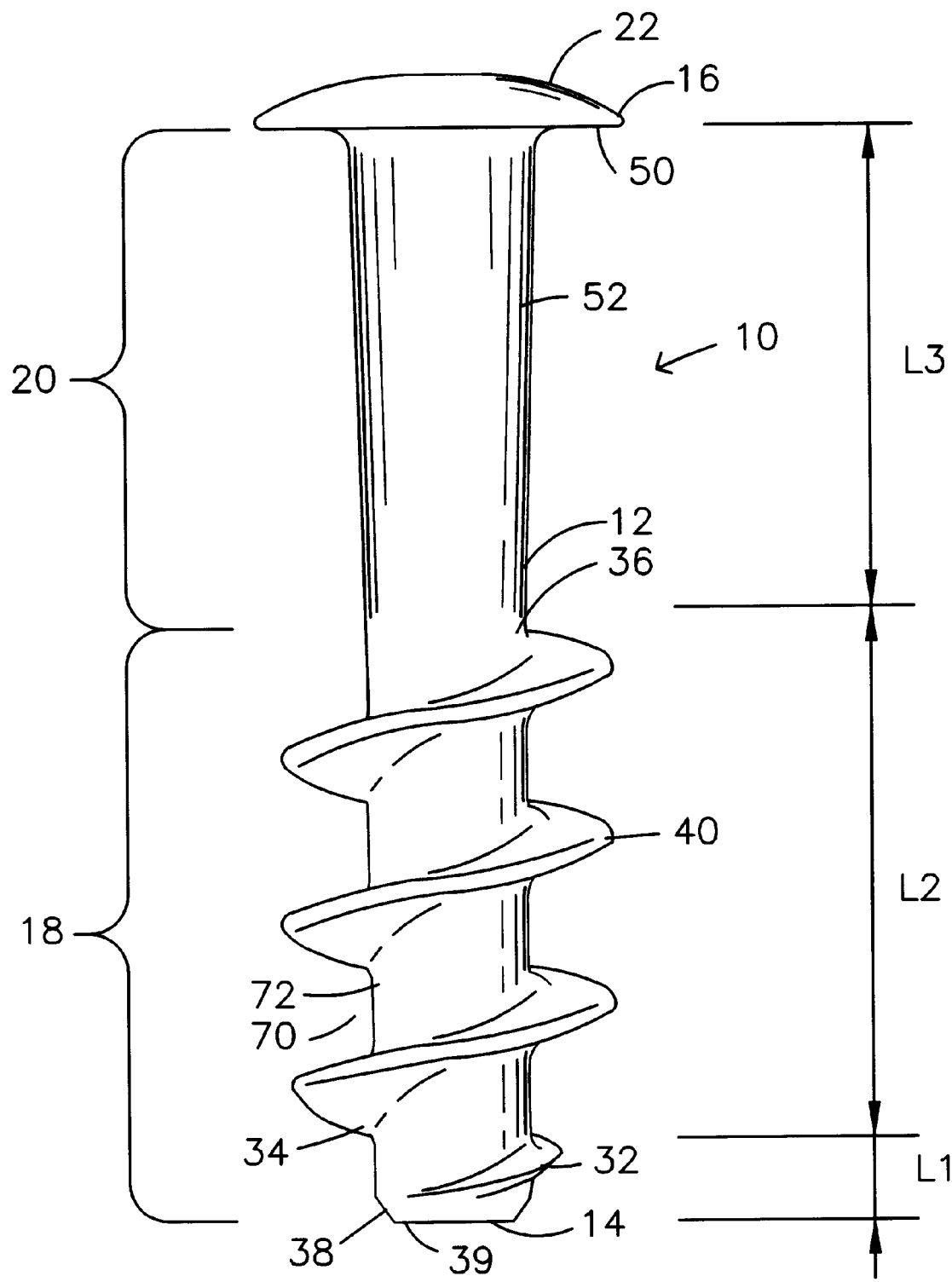
FIG. 1 is a front elevational view of a threaded soft tissue anchor constructed in accordance with the principles of this invention.
Figure 2:
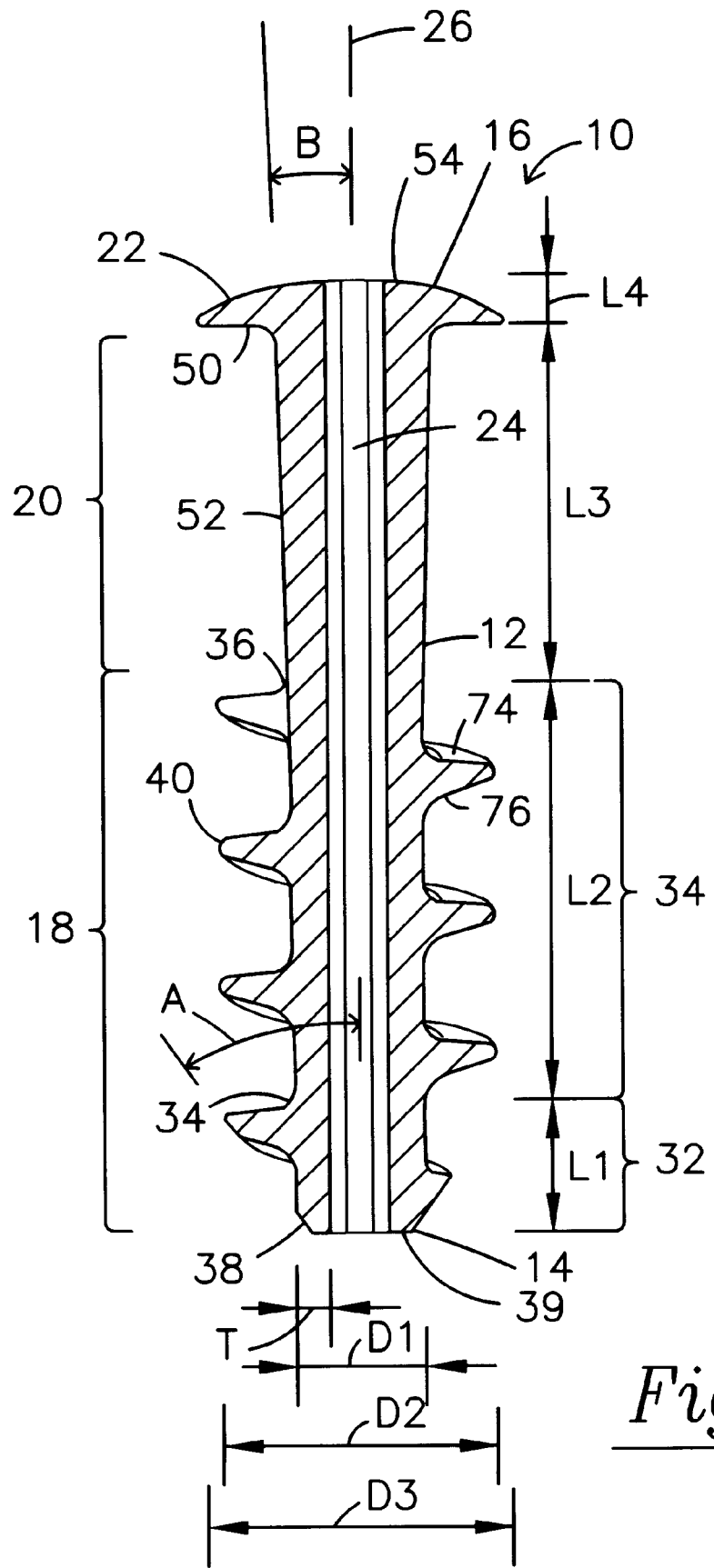
FIG. 2 is a cross-sectional view of FIG. 1.

Referring to the drawings there is shown a cannulated, bioabsorbable soft tissue anchor 10 comprising a generally cylindrical elongated body 12 having a distal end 14 and a proximal end 16. Body 12 further comprises a distal threaded section 18, a proximal non-threaded section 20, a transverse head 22 and an axial throughbore 24 aligned with axis 26. Threaded section 18 has a distal tapered portion 32, extending an axial length from distal end 14 to a point 34 on the body, and a proximal non-tapered portion 34 extending from point 34 to point 36 on the body. (Note that "points" 34 and 36 are actually transverse planes defining the boundaries between the sections.) Tapered threaded portion 32 is angled at an angle A relative to axis 26 and the axial position of the junction of the tapered thread portion and the non-tapered thread portion, i.e. point 34, is dependent upon the angle A and the major diameter of the threads. In the preferred embodiment, the distal end of tapered thread portion 32 terminates in a conical annular section 38 to minimize the cross-section of the distally facing annular surface 39 of the anchor. That is, the wall thickness T of the body 12 is decreased along the conical section 38, as best seen in FIG. 2, to produce a "sharper" annular surface to minimize resistance to the anchor as it penetrates soft tissue and bone. The distal-most end of threads 40 is sharp enough to penetrate soft tissue and bone when the device is used as described below. The transverse size of annular surface 39, the degree of distal taper and sharpness of the thread are all parameters that may vary depending upon the particular application for which anchor 10 is designed. In the preferred embodiment, anchor 10 is designed for the repair of a rotator cuff and the threads are cancellous-type threads designed to engage the cancellous bone within the humeral head into which the anchor is designed to fit.

Distal threaded section 18 has a plurality of threads 40 extending from distal end 14 to point 36. The threads are situated along a body portion which has a uniform minor diameter D1 extending from conical section 38 to point 36. The distal tapered portion 32 extends from distal end 14 for a length L1 and the proximal end of portion 32 blends into non-tapered portion 34 which has a major diameter D2 and a length L2.

Non-threaded section 20 extends for a length L3 between point 36 and the distally facing surface 50 of transverse head 22. Section 20 has a smooth tapered surface 52 which not only accommodates the soft tissue being secured but also accommodates the cortical layer of bone at the site of implantation. Surface 52 is tapered at an angle B relative to axis 26 in order to compact soft tissue and bone for a better fit. The taper also strengthens the anchor by increasing the diameter of the body 12 adjacent head 22.

Axial throughbore 24 extends entirely through anchor 10 and is designed with a non-circular cross-section to enable driving engagement of the anchor with driver 100 which is discussed below with respect to FIGS. 4 and 5. In the preferred embodiment, the cross-section of throughbore 24, best seen in FIG. 3, comprises a triangle with rounded edges 64, 66 and 68. Alternatively, the throughbore cross-section could comprise a plurality of arcuate lobes formed by the intersection of a central, circular cross-section bore and three equiangularly spaced lobes (not shown). The smooth, non-circular structure of the driving bore 24 reduces stress concentrations in the anchor. While the preferred embodiment utilizes a throughbore 24 having a uniform size and cross-section along its entire length, it will be understood that variations of size and shape may be suitable.

Transverse head 22 is integrally formed at the proximal end of section 20 and has a smooth, rounded top surface 54 and flat distally facing surface 50. The diameter D3 of head 22 is, in the preferred embodiment, slightly greater than major diameter D2 and the axial length of the head is L4.

The thread 40 has, along the length of anchor 10, a uniform pitch sufficiently large to enable the anchor to be relatively easily turned through the soft tissue and cortical bone even though the anchor is made of relatively soft bioabsorbable material which might not normally be able to pass through a relatively small hole in the cortical shell. This pitch and the relatively large thread diameter D2 produce a generally helical channel 70 having a flat helical base surface 72 for receiving soft tissue and cortical bone as the anchor is advanced. That is, the wide pitch and deep channel enable the soft tissue and cortical shell at the site of implantation to follow the minor diameter of the anchor thus minimizing trauma to the tissue and cortical bone.

In the preferred embodiment, anchor 10 is designed for rotator cuff applications and is 0.865 inches (21.97 mm) long (i.e. L1+L2+L3+L4) with minor and major diameters D1 and D2 equal to 0.118 inches (3 mm) and 0.278 inches (7.06 mm), respectively. Angle A is approximately 35°. Length L3+L4 of non-threaded section 20 plus head 22 is 0.354 inches (9 mm) long and section 20 tapers from approximately 0.139 inches (3.53 mm) adjacent the head to 3 mm at diameter D1. The thread pitch is 0.128 inches (3.25 mm) and the length of the threads, L1+L2, equals 0.511 inches (12.98 mm). To facilitate insertion of the anchor while minimizing any tendency for it to back out after insertion, the proximally facing side 74 of the threads is angled distally at approximately 13° relative to a line perpendicular to axis 26 and the distally facing side 76 is angled proximally at approximately 20°.

Referring now to FIGS. 4 and 5, there is shown a driver 100 for driving anchor 10 into a selected site of implantation. Driver 100 comprises a handle 102, an elongated support shaft 104, sufficiently long to enable the driver to be used during an arthroscopic procedure, and a driving shaft 106 having a non-circular cross-section complementary to that of driving bore 24. In the preferred embodiment, the driving shaft is made of biocompatible material such as stainless steel (although hard plastic may be suitable) and the cross-section of shaft 106 is sized so that it will frictionally retain anchor 10 during use to prevent the anchor from inadvertently falling off the tip. The tip 110 of the driving shaft 106 is pointed in order to facilitate penetration of tissue during use of the device. As shown in FIG. 5, the length of driving shaft 106 is sufficiently long to enable it to extend entirely through and beyond anchor 10 when the anchor is fully seated on driving shaft 106. An uncovered distal end 112 extends beyond the anchor in order to be used to pierce through the rotator cuff at the spot selected for fixation and into a pre-formed hole as will be explained below.

The method of using the device and driver will be described with respect to the repair of a rotator cuff during an arthroscopic surgical procedure. It will be noted that the anchor and method enable soft tissue to be directly attached to bone without the need for any suture. As shown in FIGS. 6–8, once the site of implantation of soft tissue anchor 10 has been selected, a drill or punch 120 is used to produce a small pilot hole 122 having a diameter preferably less than that of the anchor's minor diameter D1. In the preferred embodiment, the diameter of hole 122 may be 2.5–3 mm which has been found to accommodate the 3 mm minor diameter of anchor 10. Some bone compression may account for this, but too small of a hole diameter will not accept the anchor. The driver 100 with implant 10 attached is then introduced into the body through one of the arthroscopic portals (not shown) and the tip 110 is used to pierce the tissue so the surgeon can manipulate it into position over the pilot hole 122 as shown in FIG. 7. In the preferred embodiment, end 112 is made approximately 4 mm to 7 mm longer than the anchor so that it will penetrate through the rotator cuff thereby enabling the surgeon to place the tip 110 into the pre-formed hole. Once so positioned, the driver may be simultaneously pushed and turned in order to rotatably drive the anchor threads 40 into and through the soft tissue and into the pre-formed hole to a depth sufficient to firmly engage head 22 with the surface of the tissue as shown in FIG. 8. Because the anchor is made of relatively soft bioabsorbable material such as poly L-lactic acid (PLLA), the driver end 112 is necessary to start the anchor into the soft tissue and bone. It will be apparent that the anchor may be secured with varying degrees of compression and may even be countersunk into the tissue. The absence of spikes or projections on head surface 50 enables the anchor to be turned relative to the tissue without trauma. Once secured, the smooth tapered surface 52 will be in compressive contact with the soft tissue at the aperture at the point where the anchor penetrates the tissue and in compressive contact with the cortical bone at the top portion of the pilot hole. The cancellous threads will then provide fixation of the anchor in the cancellous bone at the surgical site.

It will be understood by those skilled in the art that numerous improvements and modifications may be made to the preferred embodiment of the invention disclosed herein without departing from the spirit and scope thereof.

What is claimed is:

1. A soft tissue anchor for attaching soft tissue to a hole in a bone comprising:
   a cannulated body having a proximal end, a distal end, an axis and an axial throughbore having a non-circular cross-section, said body comprising:
   a threaded distal section extending proximally from said distal end and having a first predetermined length, the distal end of said threaded section being tapered distally;
   a non-threaded proximal section extending proximally from said threaded distal section and having a second predetermined length, said non-threaded section adapted to compressively contact said soft tissue and a predetermined portion of the wall of the hole in the bone; and
   a transverse head having an annular surface at the proximal most end of said non-threaded section for seating against said soft tissue.

2. A soft tissue anchor according to claim 1 wherein said non-threaded proximal section is tapered distally along its length from said transverse head to said threaded distal section.

3. A soft tissue anchor according to claim 1 wherein said threaded distal section has a uniform minor diameter and a uniform major diameter along its length proximal of said tapered distal end of said threaded distal section.

4. A soft tissue anchor according to claim 1 wherein said threaded distal section has a uniform minor diameter along its length.

5. A soft tissue anchor according to claim 1 wherein said distal end of said threaded section is tapered approximately 35° relative to said axis.

6. A soft tissue anchor according to claim 1 wherein the pitch of the thread of said threaded distal section is approximately 3.25 mm.

7. A soft tissue anchor according to claim 1 wherein said body has a cylindrical wall and wherein said wall at said distal end is tapered distally toward said axis.

8. A soft tissue anchor for being turned through soft tissue and into a hole in a bone to attach the soft tissue to the bone comprising:

an elongated body having a proximal end, a distal end, an axis and an axial throughbore having a non-circular cross-section, said body comprising:
- a threaded distal section extending proximally from said distal end, the distal end of said threaded section being tapered distally;
- a non-threaded proximal section extending proximally from said threaded distal section; and
- a transverse head having an annular surface at the proximal-most end of said non-threaded section for seating against said soft tissue.

9. A soft tissue anchor according to claim 8 wherein said non-threaded proximal section is tapered distally along its length from said transverse head to said threaded distal section.

10. A method for attaching relatively soft tissue to a hole in relatively hard tissue comprising the steps of:
providing a soft tissue anchor comprising:
an elongated body having a proximal end, a distal end, an axis and an axial throughbore having a non-circular cross-section, said body comprising:
- a threaded distal section extending proximally from said distal end and having a first predetermined length, the distal end of said threaded section being tapered distally;
- a non-threaded proximal section extending proximally from said threaded distal section and having a second predetermined length, said non-threaded section adapted to compressively contact said soft tissue and a predetermined portion of the wall of the hole in said hard tissue;
- a transverse head at the proximal most end of said non-threaded section for seating against said soft tissue;
providing a driver for driving said soft tissue anchor, said driver comprising an elongated driving shaft having a cross-section complementary to that of said anchor throughbore, said driving shaft having a pointed tip and a length greater than said anchor;
engaging said soft tissue anchor on said driving shaft;
piercing soft tissue with said pointed tip;
positioning said pierced soft tissue and tip over said hole;
pushing said pointed tip into said hole; and
simultaneously pushing and turning said driver to advance said anchor until said head contacts the soft tissue.

11. A method according to claim 10 wherein said relatively hard tissue has a layer of relatively hard material adjacent the surface to which said soft tissue is intended to be attached and further comprising the step of advancing said soft tissue anchor until said non-threaded surface compressively contacts said layer.

12. A soft tissue anchor system comprising a threaded soft tissue anchor for attaching a relatively soft tissue to a relatively hard tissue and a driver for turning said anchor through said relatively soft tissue and into a hole at a selected site of implantation in said relatively hard tissue, said soft tissue anchor comprising:
an elongated body having a proximal end, a distal end, an axis and an axial throughbore having a non-circular cross-section, said body comprising:
- a threaded distal section extending proximally from said distal end and having a first predetermined length, the distal end of said threaded section being tapered distally;
- a non-threaded proximal section extending proximally from said threaded distal section and having a second predetermined length, said non-threaded section adapted to compressively contact said soft tissue and a predetermined portion of the wall of the hole in the bone; and
- a transverse head at the proximal most end of said non-threaded section for seating against said soft tissue; and
said driver comprising:
- an elongated driving shaft having a cross-section complementary to that of said anchor throughbore, said driving shaft having a pointed tip and a length greater than said anchor; and
- a handle for manipulating said driving shaft.

* * * * *